US008759753B1

(12) United States Patent
Di Bussolo et al.

(10) Patent No.: US 8,759,753 B1
(45) Date of Patent: Jun. 24, 2014

(54) METHODS AND APPARATUS FOR IMPROVED IMMUNOSUPPRESSANT DRUG MONITORING

(71) Applicants: Joseph M. Di Bussolo, West Chester, PA (US); Marta Kozak, Palo Alto, CA (US)

(72) Inventors: Joseph M. Di Bussolo, West Chester, PA (US); Marta Kozak, Palo Alto, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 13/830,103

(22) Filed: Mar. 14, 2013

(51) Int. Cl.
 B01D 59/44 (2006.01)
 B01D 15/08 (2006.01)
 H01J 49/00 (2006.01)

(52) U.S. Cl.
 USPC ........ 250/282; 250/288; 210/635; 210/198.2; 536/25.41; 73/1.02

(58) Field of Classification Search
 USPC ...................... 250/282, 288; 210/635, 198.2; 536/25.41; 73/1.02
 See application file for complete search history.

(56) References Cited

U.S. PATENT DOCUMENTS

| 7,425,700 B2 * | 9/2008 | Stults et al. ................ 250/288 |
| 7,815,803 B2 * | 10/2010 | Kobold et al. ............... 210/635 |
| 7,906,758 B2 * | 3/2011 | Stults et al. ................ 250/282 |

OTHER PUBLICATIONS

Thermo Scientific, "Thermo Scientific ClinSpec™ Immunosuppressants Test," Thermo Scientific Product Insert, ClinSpec Immunosuppressants Test Kit (launched at 2010 ASMS), pp. 1-3.

* cited by examiner

Primary Examiner — Nikita Wells
(74) Attorney, Agent, or Firm — Thomas F. Cooney (57) ABSTRACT

A method for assaying one or more immunosuppressant drug analytes in a sample derived from whole blood comprises: (a) passing the sample dissolved in a mobile phase through a length of 30 mm or less of a stationary phase of a reversed-phase chromatographic column; (b) eluting the separated analytes from the reversed-phase chromatographic column; (c) ionizing molecules of the eluted separated analytes by a heated electrospray ionization source of a mass spectrometer so as to generate a plurality of precursor ion species; (d) isolating, for each analyte, a respective one of the precursor ion species; (e) fragmenting ions of each of the isolated precursor ion species in a fragmentation cell of the mass spectrometer so as to generate a plurality of product ions therefrom; and (f) detecting, for each analyte, the presence and quantity of a respective one of the product ion species using a detector of the mass spectrometer.

11 Claims, 5 Drawing Sheets

METHODS AND APPARATUS FOR IMPROVED IMMUNOSUPPRESSANT DRUG MONITORING

FIELD OF THE INVENTION

This invention relates to assays of drugs in biological samples and, more particularly, to assays of immunosuppressant drugs in whole blood by liquid chromatography coupled to mass spectrometry.

BACKGROUND OF THE INVENTION

In certain circumstances, the immune system must be controlled in order to either augment a deficient response or suppress an excessive response. For example, when organs such as kidney, heart, lung, bone marrow, and liver are transplanted in humans, the body will sometimes reject the transplanted tissue by a process referred to as allograft rejection. In treating allograft rejection, the immune system is frequently suppressed in a controlled manner through drug therapy with immunosuppressant drugs including, but not limited to, cyclosporin, tacrolimus, sirolimus, mycophenolic acid, and everolimus. Immunosuppressant drugs are carefully administered to transplant recipients in order to help prevent allograft rejection of the foreign (i.e. non-self) tissue. Many of the immunosuppressant drugs require the measurement of their concentrations in blood with subsequent dosage adjustment to maximize efficacy while minimizing toxicity. Thus, regular monitoring of immunosuppressant drug blood levels is an essential component of the post transplant medical regimen.

Traditionally, immunosuppressant drug monitoring has been performed using immunoassays. However, there exist some known immunosuppressant drug assays which employ tandem mass spectrometry coupled to liquid chromatography, the technique sometimes known as LC-MS/MS. Generally speaking, (LC-MS/MS) is an extremely useful technique for detection, identification and (or) quantification of components of mixtures or of analytes within mixtures. Specifically, this technique has further been found to be a powerful analytical tool that provides high specificity and sensitivity in measurement of immunosuppressant drugs. Because of a relatively simple sample preparation procedure and high sensitivity and specificity, LC-MS/MS has shown great potential to be the method of choice for measuring immunosuppressant drugs, especially for simultaneous multiple-drug monitoring.

In general, liquid chromatography coupled with mass spectrometry (the general technique known as LC-MS) provides data in the form of a mass chromatogram, in which detected ion intensity (a measure of the number of detected ions) as measured by a mass spectrometer is given as a function of time. In the LC-MS technique, various separated chemical constituents elute from a chromatographic column as a function of time. As the various constituents are eluted from the column, they are submitted for mass analysis by a mass spectrometer. The mass spectrometer accordingly generates, in real time, detected relative ion abundance data for ions produced from each eluting analyte, in turn.

Mass spectrometry (MS) is an analytical technique to filter, detect, identify and/or measure compounds by the mass-to-charge ratios of ions formed from the compounds. The quantity of mass-to-charge ratio is commonly denoted by the symbol "m/z" in which "m" is ionic mass in units of Daltons and "z" is ionic charge in units of elementary charge, e. Thus, mass-to-charge ratios are appropriately measured in units of "Da/e". Tandem mass spectrometry (MS/MS) techniques generally include (1) ionization of compounds to produce ion species of different respective m/z ratios; (2) selection and isolation of one (or a few) specific ion species; (3) fragmentation of the selected ion species so as to generate product ions; and (4) detection and analysis of the mass-to-charge ratios of particular diagnostic fragment ion species; and determination of analyte abundances in the original sample from measured quantities of the diagnostic fragment ion species.

Immunosuppressant drugs (ISDs) are often analyzed in whole-blood using LC-MS or LC-MS/MS. For example, one known quantitative assay for the research-use only determination of the ISD compounds Cyclosporin A, Sirolimus, Tacrolimus and Everolimus in whole blood specimens is provided by the ClinSpec™ Immunosuppressants Test kit provided by Thermo Scientific of Waltham Mass. USA. Sample preparation is based on simple protein precipitation. Whole blood samples are treated with a provided extraction solution to precipitate protein and extract the compounds of interest into the organic phase. The supernatant from the protein precipitated whole blood sample is then injected onto a column provided with the kit. The analyte(s) of interest as well as provided internal standards are then eluted into the ionization source of the mass spectrometer.

The chromatographic analytical column used in this known ClinSpec™ assay is a C8 reverse-phase high-performance liquid chromatography (HPLC) column (specifically a 10 mm long Thermo Scientific Javelin™ guard column packed with Thermo Scientific Hypersil Gold™ 5 μm particles. An atmospheric pressure chemical ionization (APCI) ion source is used in positive-ion mode in the mass spectrometer. The precursor ion species for Tacrolimus, Sirolimus and Cyclosporin A and Everolimus are at m/z ratios of 821.4, 931.6, 1219.9 and 975.7, respectively. The monitored product ions formed by fragmentation of these parent ion species are at m/z ratios of 768.3, 864.5, 1202.9 and 908.4, respectively. Ascomycin and Cyclosporin D are used as internal standards.

Although the above-described ISD assay utilizes an APCI source, the use of heated electrospray (H-ESI) ionization could improve the sensitivity of the assay. Further, many analytical or clinical laboratories are set up to routinely perform LC-MS analyses using electrospray ionization and would suffer inconvenience or decreased efficiency from having to re-configure and or re-calibrate their systems for APCI. Unfortunately, a difficulty arises in the use of electrospray ionization in conjunction with mass spectrometry of ISDs from clinical samples. This difficulty arises from the co-elution of phospholipids. Since the phospholipids have similar hydrophobicity characteristics to the ISD analyte compounds, they are chromatographically separated only with difficulty from the analytes. The problem when using electrospray ionization is that the co-eluting phospholipids causes strong ion suppression of the analyte compounds. The general phenomenon of ion suppression during electrospray ionization has been shown (King R, et al., "Mechanistic investigation of ionization suppression in electrospray ionization", J Am Soc Mass Spectrom 2000; 11:942-50) to result from a change in the efficiency of droplet formation or droplet evaporation in the presence of the non-volatile or less volatile interfering compound, thereby reducing the quantity of analyte ions that are formed.

The conventional approach to eliminating the problem of ion suppression of ISDs in the presence of co-eluting phospholipids would be to improve the chromatographic separation of these two types of compounds, either by installing a second "cleanup" column upstream from the analytical column or by increasing the length of the analytical column. However, the inventors have discovered that installing a commonly-used TurboFlow™ High-Turbulence Liquid Chromatography cleanup column does not sufficiently separate phospholipids from ISD compounds as a result of the similar hydrophobicities of these two types of compounds. The inventors have also discovered that, somewhat surprisingly, increasing the length of the analytical column from its conventional length of 50 mm in fact exacerbates the problem of ion suppression by co-eluting phospholipids.

Accordingly, there is a need in the art for improved techniques—both apparatus and methods—for performing LC-MS assays of immunosuppressant drugs in patient samples using electrospray ionization. Such methods must eliminate ion suppression from unwanted matrix components such as phospholipids. Although stable isotopes for each ISD are available to compensate for interferences, it is best to minimize such interferences, in order to maintain analysis accuracy at low concentration levels and to maintain a reliable lower limit of quantitation of these compounds.

SUMMARY OF THE INVENTION

The inventors have discovered that the phospholipids are so strongly partitioned onto the stationary phase of reverse-phase analytical columns that the conventional cleaning or washing steps that are generally included between chromatographic runs are insufficient to totally remove all bound phospholipids from the column. The residual phospholipids, being thus dispersed through the column prior to another chromatographic separation, cause carryover effects resulting in broad elution of these interfering compounds over a range of retention times. The inventors have further discovered that, somewhat surprisingly, using an analytical column of a relatively short length can give adequate separation of the phospholipids from the ISDs, with elimination of ion suppression, since the short columns may be adequately purged of residual phosphipids between runs.

Accordingly, a method for assaying one or more immunosuppressant drug analytes in a sample derived from whole blood is provided, the method comprising: (a) passing the sample dissolved in a mobile phase through a length of 30 mm or less of a stationary phase of a reversed-phase chromatographic column so as to separate the analytes from one another; (b) eluting the separated analytes from the reversed-phase chromatographic column; (c) ionizing molecules of the eluted separated analytes by a heated electrospray ionization source of a mass spectrometer so as to generate a plurality of precursor ion species; (d) isolating, for each analyte, a respective one of the precursor ion species; (e) fragmenting ions of each of the isolated precursor ion species in a fragmentation cell of the mass spectrometer so as to generate a plurality of product ions therefrom; and (f) detecting, for each analyte, the presence and quantity of a respective one of the product ion species using a detector of the mass spectrometer. The analytes may comprise one or more of the compounds everolimus, sirolimus, tacrolimus and cyclosporin A and the method may further comprise adding internal standards $^{13}CD_2$-tacrolimus and $D_{12}$-cyclosporin A to the sample, the presence of these internal standards being monitored by the mass spectrometer for the purpose of quantifying the analytes. In various embodiments, the step (a) may comprise passing the sample dissolved in the mobile phase through a stationary phase comprising an 8-carbon alkyl chain material bonded to 2.6 µm diameter particles having solid silica cores surrounded by porous silica outer layers. The length of the stationary phase through which the sample is passed may be 30 mm or less. In various embodiments, the mobile phase may comprise a mixture of a first solvent (MPA) comprising water+10 mM ammonium formate+0.05% formic acid and a second solvent (MPB) comprising methanol+10 mM ammonium formate+0.05% formic acid, wherein the composition of the mobile phase mixture varies from 30% MPA and 70% MPB to 0% MPA and 100% MPB during the separating and eluting of the analytes. Various embodiments may further include washing the reversed-phase chromatographic column with the MPB solvent to remove phospholipids from the column. Various embodiments may further comprise passing the sample into and out of a high turbulence liquid chromatography column prior to performing the step (a) so as to remove non-analyte compounds from the sample.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-4, taken in conjunction with the following description.

Figure 1A:
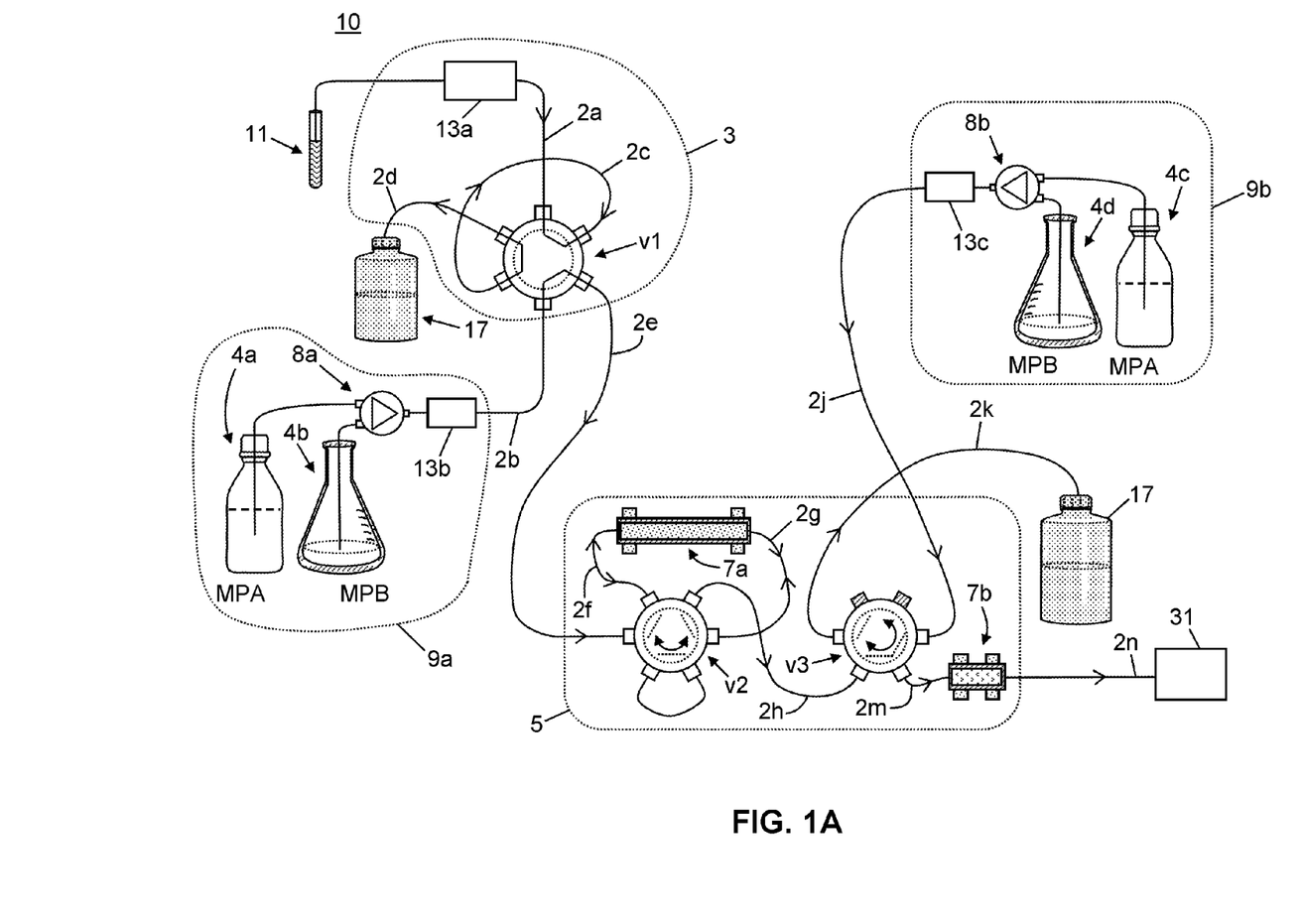
FIG. 1A is a schematic illustration of an embodiment of a liquid chromatograph apparatus in accordance with the present teachings.

FIG. 1A is a schematic illustration of a exemplary liquid chromatography system in accordance with the present teachings. The system 10 shown in FIG. 1A may be conceptually viewed as comprising a sample injector sub-system 3, a chromatography sub-system 5, mobile-phase supply systems 9a and 9b, a mass spectrometer 31, various fluid tubing lines 2a-2n and one or more waste containers 17. This modular view of the system 10 does not necessarily imply a corresponding structural modularity although such structural modularity is not excluded. Although two mobile-phase supply systems are shown, a single mobile-phase supply system accompanied by fluid flow routing valves might also be employed.

The chromatography sub-system 5 comprises two chromatographic columns 7a, 7b. A first chromatographic column 7a (a "cleanup" column) is provided for conducting an initial separation of a sample-containing liquid chemical mixture so as to isolate a sub-group of its constituent substances. A second chromatographic column 7b (an "analytical" column) is also provided for performing a more finely resolved or finely detailed separation of the constituents of the isolated sub-group.

The chromatography sub-system 5 further comprises a valve system which, as illustrated, may comprise two multiple-port valves v2, v3. The multiple-port valves may comprise 6-port valve of a type commonly used in chromatographic systems. As is known, such 6-port valves may be employed in either one of two different configurations: a first configuration in which the first, third and fifth ports are respectively fluidically coupled to the second, fourth and sixth ports and a second configuration in which the first, third and fifth ports are respectively fluidically coupled to the sixth, second and fourth ports. For example, the illustrated valve system may comprise two multiple-port rotary valves v2, v3 such as the valves known as Rheodyne valves sold by IDEX Health & Science, 619 Oak Street Oak Harbor, Wash. USA.

The valves v2, v3 are fluidically interconnected, by means of various fluid tubing lines, to one another, to the two columns 7a, 7b, to the sample injector sub-system 3, to the mobile-phase supply systems 9a and 9b and to the mass spectrometer 31. The valve system shown in FIG. 1A is capable of: (a) transferring a portion of a sample-containing fluid (e.g., a mixture of sample and solvents provided from supply system 9a) to the first column 7a along fluid tubing line 2f; (b) isolating and concentrating a sub-group of sample constituent substances on the first column 7a while other unwanted constituents are transferred to waste 17 along fluid tubing lines 2g, 2h and 2k, (c) mixing the isolated and concentrated constituents with solvent fluids or a mobile phase provided from supply system 9b, (d) transferring the isolated and concentrated sub-group of constituent substances and mobile phases to the second column 7b along fluid tubing line 2m and (e) causing the sub-group of constituent substance to flow through the second column 7b so as to be further separated therein. The separated chemical constituents eluting from the second column 7b are transferred to the mass spectrometer 31 along fluid tubing line 2n. The mass spectrometer 31 serves as a detector for detecting or identifying the separated constituent substances as they are received, in sequence from the second column 7b. The fluid tubing lines 2f and 2g are both shown with bi-directional arrows because, under some circumstances, sample fractions previously concentrated in the first cleanup column 7a may be released from the column and transferred back to the valve v2 by back-flushing the column with solvent in the reverse flow direction from that used to load sample onto the column.

The sample injector sub-system 3 comprises another multiple-port valve v1 which is fluidically coupled to the mobile-phase supply system 9a by means of fluid tubing line 2b. The mobile-phase supply system 9a comprises at least two sources of mobile-phase solvents which, in this example, are the two solvents denoted as "Mobile Phase A" (MPA) in solvent source 4a and "Mobile Phase B" (MPB) in solvent source 4b. A fluid pump 13b may provide impetus to deliver one or the other of MPA or MPB or any mixture thereof in any proportion to multiple-port valve v1 through fluid tubing line 2b. The mixed proportions of (or the selection between) MPA and MPB may be controlled by a first gradient valve 8a that is fluidically coupled between the fluid pump 13b and the solvent sources 4a, 4b.

One port of the multiple-port valve v1 of the injector sub-system 3 is fluidically coupled to valve v2 of the chromatography sub-system 5 by means of fluid tubing line 2e. As shown, a first port of the valve $v^1$ is fluidically coupled to a sample contained in a sample source 11 by means of fluid tubing line 2a. The sample may be delivered to the valve v1 under the impetus of a fluid pump 13a. Another port of the valve (in this example, the fourth port) is fluidically coupled to the mobile-phase supply system 9a by means of fluid tubing line 2b. Two ports of the multiport valve v1 are fluidically coupled, respectively, to the two ends of a looped fluid tubing line 2c which may be used for temporary storage of a portion of the sample prior to its being mixed with one or more of the mobile phase solvents. Another port of the multiport valve v1 is fluidically coupled to a waste container 17 by means of fluid tubing line 2d. It should be noted that the terms "fluid tubing", "fluid tubing line", "fluid tubing segment" and similar terms as used herein are not intended to necessarily limit the embodiments to the use of tubing portions, in a strict sense, but are meant to include other alternative forms of fluid transfer lines or passageways such as, for example, channels or grooves in plates or bores in solid components.

The second mobile-phase supply system 9b, if present, comprises solvent sources solvent sources 4c and 4d. These solvent sources may contain the same solvents MPA and MPB as provided by solvent sources 4a and 4b. Alternatively, in some embodiments, the solvents contained in solvent sources 4c and 4d may be different from those provided in solvent sources 4a and 4b. The second mobile-phase supply system 9b, further comprises a gradient valve 8b which may select flow of one of the other of the two solvents provided from solvent sources 4c and 4d or which may mix the flows of the two solvents from solvent sources 4c and 4d in any proportion. The solvents provided from the mobile-phase supply system 9b are provided to a port of the valve v3 of the chromatography sub-system 5.

During the operation of a sampling step of the system 10 (FIG. 1A), the valve v1 of the sample injector sub-system 3 is configured such that a portion of the sample is drawn from the sample source 11, under the action of fluid pump 13a, so as to fill the looped tubing 2c. Then, in a subsequent column loading step, the valve v1 is configured such that the sample portion is mixed with solvents from the mobile-phase supply system 9a and expelled from looped tubing 2c under the action of the fluid pump 13b. During this loading step, the expelled mixture of sample and solvents is routed through fluid tubing 2e to the valve v2 of the chromatography sub-system 5.

During the column loading step, the valve v2 is configured such that the expelled mixture of sample and solvents is delivered to the first column 7a (the "cleanup" column). During this step, the mobile phase composition and the stationary phase composition of the column 7a may be such that analytes of interest are retained within the first column 7a while a variety of unwanted sample pass through the column. In this situation, the valve v3 may be configured such that the unwanted compounds are flushed to waste container 17. The retained analyte compounds will subsequently be transferred to the second column (the "analytical" column) 7b by appropriate re-configuration of the valves v2 and v3 and change of the mobile phase composition. Alternatively, the mobile phase and stationary phase compositions may be such that the unwanted compounds are retained within the cleanup column while the analytes of interest pass through the column. In this alternative situation, the valve v3 may be configured such that the analyte compounds pass directly into the second column 7b.

The solvents plus analytes pass through the valve v3 during their transfer from the cleanup column 7a to the analytical column 7b. During this step, the composition of the solvents (the mobile phase) should be such that the analyte compounds are retained on the analytical column 7b. In order to adjust the mobile phase composition so as to facilitate such retention on the column 7b, the solvents and analyte compounds that enter valve v3 from fluid tubing line 2h may be mixed, within valve v3, with solvents of a different composition that enter the valve v3 from fluid tubing line 2j. Such mixing at or within the valve v3 is possible if the valve is of a known type that has an internal channel configuration such that three immediately adjacent valve ports may be simultaneously fluidically intercoupled.

After the retention of analyte compounds on the analytical column 7b, operation of the system 10 (FIG. 1A) further proceeds by an elution step during which the retained analytes are released from the column stationary phase and proceed through the column at different rates so as to exit the column at different respective retention times. During this elution step, a mobile phase of a composition such that the retained analytes are released from the stationary phase is provided from the mobile-phase supply system 9b through the fluid tubing line 2j. During the course of elution, the mobile phase composition may be changed, either stepwise or continuously, by varying the relative proportions of solvents MPA and MPB mixed by gradient valve 8b. The eluted analyte compounds pass to the mass spectrometer 31 through fluid tubing line 2n. The mass spectrometer serves as a detector for sensing the presence of analytes, verifying their identity and quantifying their original concentrations.

In preferred embodiments, the first column 7a may comprise a TurboFlow™ column commercially available from Thermo Scientific of Waltham Mass. USA. Optionally, however, the first column 7a may comprise another form of cleanup column such as a Solid Phase Extraction column or an affinity chromatography column. A TurboFlow™ column, which is generically referred to as a High-Turbulence Liquid Chromatography or HTLC column, may be employed to isolate and possibly concentrate a subset of compounds based on their size range or molecular weight range. Such columns are described in detail in U.S. Pat. Nos. 5,772,874; 5,919,368 and 6,149,816, all of which are hereby incorporated by reference in their entirety as if fully set forth herein. Briefly stated, the TurboFlow™ apparatus and methods include or relate to a chromatography column or body that is formed as a substantially uniformly distributed multiplicity of rigid, solid, porous particles having substantially uniform mean cross-section dimensions or diameters of not less than about 30 μm, typically 50 μm or greater up to, but not limited to, 1000 μm in certain instances. The particles are selected from a range of various sizes and shapes and are held together in a body or column as by pressure, sintering and the like so that interstitial channels having a total interstitial volume of not less than about 45% of the total volume of the column are formed between the particles. The surfaces of the particles, including the inner surfaces of the pores in the particles, are chromatographically active, as by being coated with chromatographic stationary phase layers.

In various embodiments, the analytical column 7b may comprise a reverse-phase column. The analytical column 7b is preferably shorter than 40 mm in length in order to permit adequate post-analysis removal of interfering and co-eluting phospholipids so as to prevent carryover from sample to sample. The column "length" as noted above refers to the length of a volume of a column container in which stationary phase is contained or disposed. The actual distance traveled by a parcel of fluid within the column may, of course, be much greater than the length as defined above, as a result of pore structure and tortuousity. In some preferred embodiments, the analytical column 7b may comprise a specific type of reverse-phase column known as an Accucore™ C8 column commercially available from Thermo Scientific of Waltham Mass. USA. Specifically, the stationary phases of Accucore™ columns use particles having 2.6 μm solid-core material and having a very tight particle size distribution. The particles can be described as a solid silica core surrounded by a porous outer layer. The very tight particle size distribution of this material results in columns with high permeability, and, therefore, for the same nominal pressure, better chromatographic separations are achieved than those utilizing fully porous materials. The solid-core and the well defined porous outer layer provides shorter diffusion paths into the stationary phase compared with those in fully porous particles, thus reducing band broadening and improving separation efficiency.

Figure 1B:
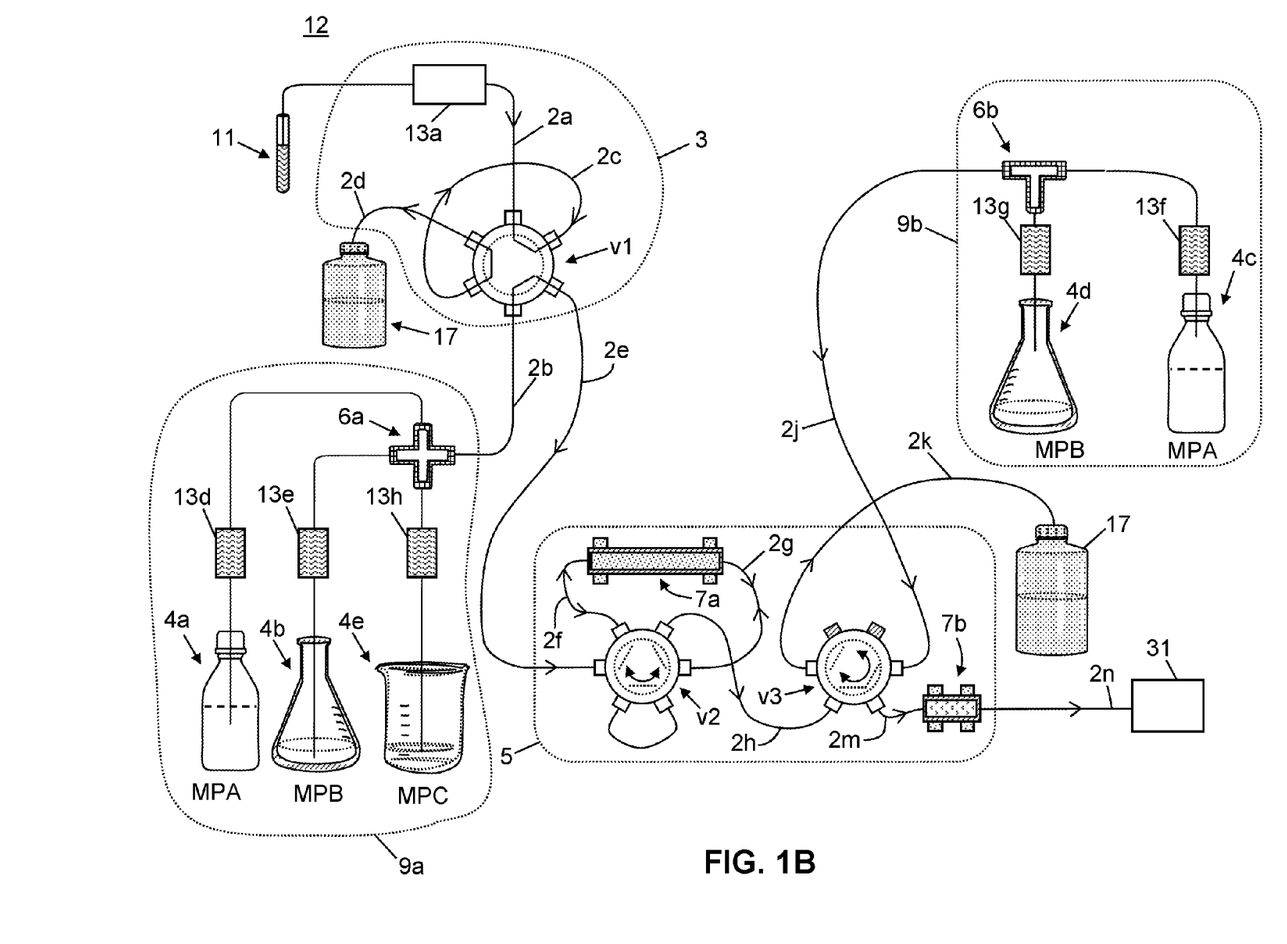
FIG. 1B is a schematic illustration of an alternative embodiment of a liquid chromatograph apparatus in accordance with the present teachings.

FIG. 1B is a schematic illustration of a second liquid chromatography system in accordance with the present teachings. Many of the components of the system 12 shown in FIG. 1B are similar to similarly numbered components of the system shown in FIG. 1A and their descriptions are not repeated here. However, the system 12 (FIG. 1B) does comprise several modifications in comparison to the system 10 (FIG. 1A). The modified aspects need not occur all together; some modifications could be implemented individually or the modifications could be implemented in various combinations with one another. In contrast to the system 10 illustrated in FIG. 1A, the system 12 (FIG. 1B) includes a mobile-phase supply system 9a that includes an extra solvent ("Mobile Phase C" or MPC) in solvent source 4e in addition to the previously-described mobile phase solvents MPA and MPB. Thus, the embodiment shown in FIG. 1B comprises three solvents in mobile-phase supply system 9a and two solvents in mobile-phase supply system 9b. Generally, however, the number of different solvents used need not be limited to any particular quantity. The MPC solvent may be employed, by way of non-limiting example, as a washing agent to clean the columns and tubing between assays.

The system 12 shown in FIG. 1B further differs from the system 10 of FIG. 1A in that each one of the solvent sources is associated with its own respective syringe pump. Thus, syringe pumps 13d, 13e and 13h are configured to draw solvents from solvent sources 4a, 4b and 4e, respectively and syringe pumps 13f and 13g are configured to draw solvents from solvent sources 4c and 4d, respectively. The syringe pumps may be designed so as to contain liquid volumes designed for a single push per sample analysis. For example, each syringe pump may be limited to holding 3.0 mL of liquid. Such a configuration greatly reduces the wear and tear associated with traditional reciprocating pumps whose pistons can move several hundred if not thousands of times per sample run.

Since the flow rates of the various solvents dispensed from the syringe pumps can by accurately controlled by operation of the pumps, the gradient valves of the system 10 are replaced, in the system 12, by simple mixing junctions. In the embodiment shown, a fluidic junction 6a which, in this instance, comprises a mixing cross junction, is able to direct any of the solvents from solvent sources 4a, 4b and 4e into fluid tubing line 2b. The proportions of solvents MPA, MPB and MPC flowing as a mixture through fluid tubing line 2b are controlled by the operation of the syringe pumps 13d, 13e and 13h. In similar fashion, second fluidic junction 6b which, in this instance comprises a mixing tee junction, is able to direct either of the solvents from solvent sources 4c and 4d into fluid tubing line 2j. Check valves (not shown) may be employed to prevent solvents from flowing out an incorrect port of the mixing junctions 6a, 6b.

Note that, in alternative embodiments, a single source container of the solvent MPA could replace the two solvent sources 4a and 4c illustrated in either FIG. 1A or FIG. 1B. In various embodiments, a single source container of the solvent MPB could replace the two solvent sources 4b and 4d illustrated in either FIG. 1A or FIG. 1B.

Figure 2:
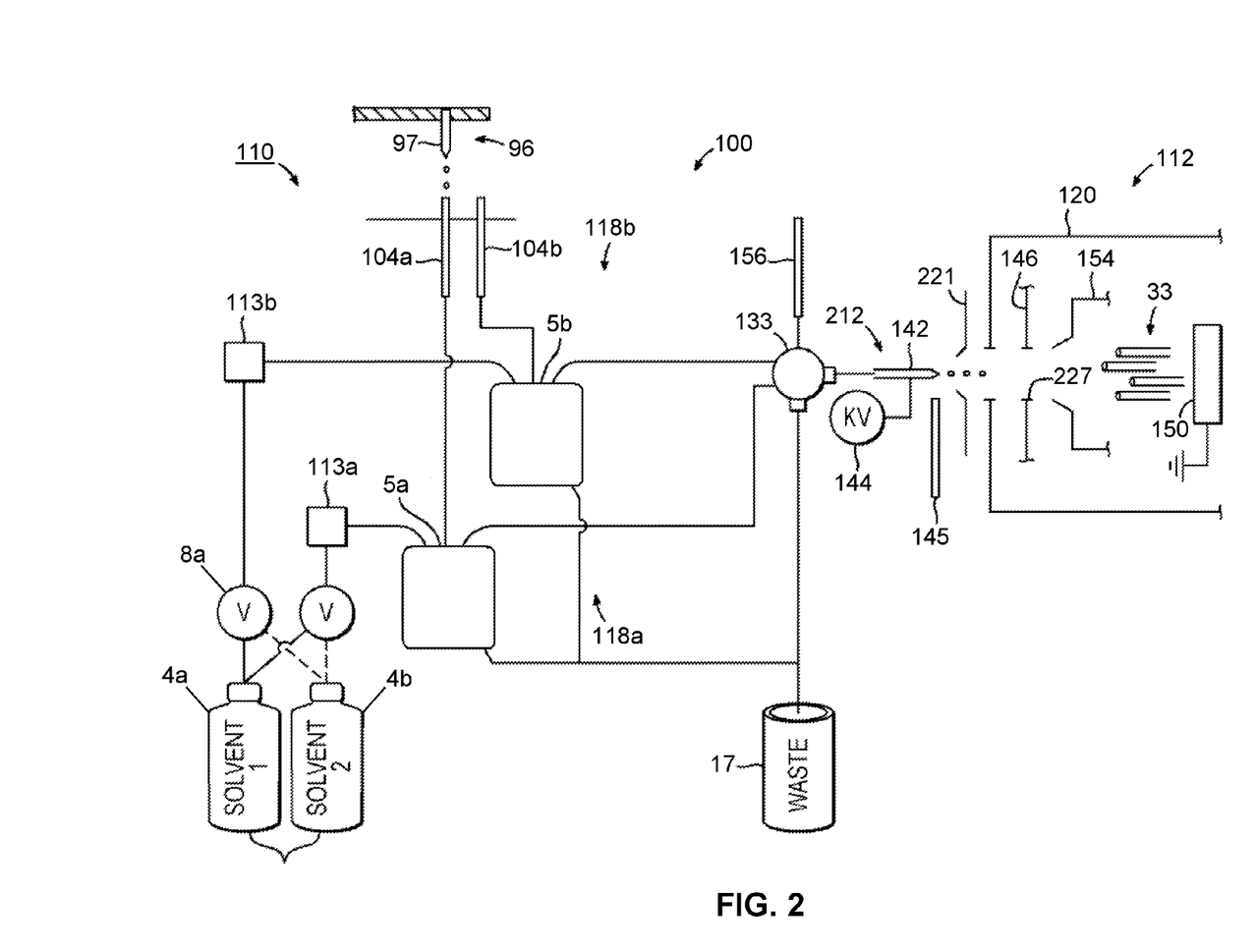
FIG. 2 is a schematic view of a liquid chromatography (LC) and mass spectrometry system an automated sample analysis system in accordance with one embodiment of the present teachings wherein the system comprises two LC channels operating in parallel.

FIG. 2 illustrates one embodiment of an LCMS system on which the invention may be practiced. The system 100 comprises a multiple-channel liquid chromatography station 110 and a mass spectrometer station 112 that is able to receive sample material from any of the LC channels 118a, 118b. The liquid chromatography station 110 (referred to hereinafter as "LC station" 110) may include one, two, or more injection ports 104a, 104b for accepting aliquots of prepared samples. The injector ports may receive samples for analysis, by way of non-limiting example, from a pipette or syringe 97 of an automated robotic sampling assembly 96. In some embodiments, the robotic sampling assembly 96 may further include sample preparation components, such as a supply of lysing agent and a dispenser for adding the lysing agent to to whole blood samples, a heater to provide thermal energy to promote reactions within samples, a centrifuge to cause precipitation of certain components from samples, a supply of internal standards and one or more dispensers for spiking the internal standards into samples, etc. The robotic sampling assembly, including any such sample preparation components, may operate automatically under computer control, so as to perform the same (or similar) sample preparation steps described in the "Materials and Methods" section of this document. One such automated sample preparation assembly is described in co-pending international (PCT) patent publication WO2012058632 A1 titled "Automated System for Sample Preparation and Analysis" and having an international filing date of Oct. 28, 2011, said international application incorporated herein by reference in its entirety.

The injection ports 104a, 104b may be connected on-line to one or more chromatography columns for separation of the prepared sample into analytes of interest eluting at one or more elution times and a plurality of ancillary or waste eluents. The LC station 110 shown in FIG. 2 may includes two or more separation channels, e.g., the LC channels 118a, 118b. Either one or both of the two LC channels 118a, 118b illustrated in FIG. 2 may receive prepared sample material from a respective one of the injection ports 104a, 104b and may include a respective instance of the chromatography sub-system 5 (comprising valves v1 and v2 and columns 7a, 7b as described above). In the example shown in FIG. 2, the first channel 118a includes a first such instance 5a of the chromatography sub-system and the second channel 118b includes a second such instance 5b. Alternatively, only one of the LC channels may include the particular columns 7a, 7b described above whereas the other one of the channels comprises a different set of columns adapted to analyze a different class of analytes other than ISDs.

In some embodiments the two columns 7a, 7b of one or more of the chromatography sub-systems 5a, 5b may be provided as a matched set within a single replaceable two-column cartridge. One suitable two-column cartridge configuration is disclosed in co-pending international (PCT) patent publication WO2012058515 A2 "Modular Multiple-Column Chromatography Cartridge" and having an international filing date of Oct. 28, 2011, said international application incorporated herein by reference in its entirety.

Each of the two LC channels 118a, 118b is associated upstream with a respective injector ports 104a, 104b and associated downstream with a single mass spectrometer 31 of the mass spectrometer station 112 in a manner that enables multiplexing or staggered sample introduction of samples into the mass spectrometer 31. The multiple-chromatography-channel configuration shown in FIG. 2 increases analytical throughput in comparison to single-channel systems.

Each of the two or more LC channels (in this example, channels 118a, 118b) may be associated with its own respective set of solvent sources. Alternatively, the two channels may share a single set of solvent sources, such as the shared solvent sources 4a, 4b illustrated in FIG. 2. Each of the LC channels may include its own respective set of fluidic pumps so as to draw solvents (e.g. mobile phases) from the solvent sources and to propel samples dissolved in the solvents through the valves and columns of the respective chromatography sub-system, such as the sub-system 5a and the sub-system 5b shown in FIG. 2. In the system 100, the set of fluidic pumps 113a performs these functions within the channel 118a and the set of fluidic pumps 113b performs these functions within the channel 118b. Each such set of pumps may include multiple pumps, such as the various pumps illustrated in either FIG. 1A or FIG. 1B. In some embodiments, the pumps may comprise syringe pumps with volumes designed for a single push per sample analysis, thereby greatly reducing the wear and tear associated with traditional reciprocating pumps whose pistons can move several hundred if not thousands of times per sample run.

The LCMS system 100 may include a separate injection port 156 that is associated with the selection valve 133 and therefore by-passes the LC channels 118a, 118b. The injection port 156 may be used for injecting a calibration standard or a control standard for performing a calibration or control analysis respectively as appropriate. For clarity of discussion of the mass spectrometer 31 hereafter, only the prepared sample injections will be discussed. Yet it will be understood that a sample calibration standard or control standard injected via the injection port 156 would be analyzed in a similar manner.

The injected, prepared sample moves through the columns 7a, 7b (not specifically illustrated in FIG. 2) of either the chromatography sub-system instance 5a or the sub-system instance 5b in the manner described previously in this document. The eluents and analytes from both of the first and second LC channels 118a, 118b are directed into the selection valve 133 where the eluents are directed into the waste container 134 while the analytes are directed to an ionization source 212 of the mass spectrometer station 112. The configuration of the selection valve 133 may also determine which one of the two channels provides analytes to the mass spectrometer 31 at any given time.

Figure 3:
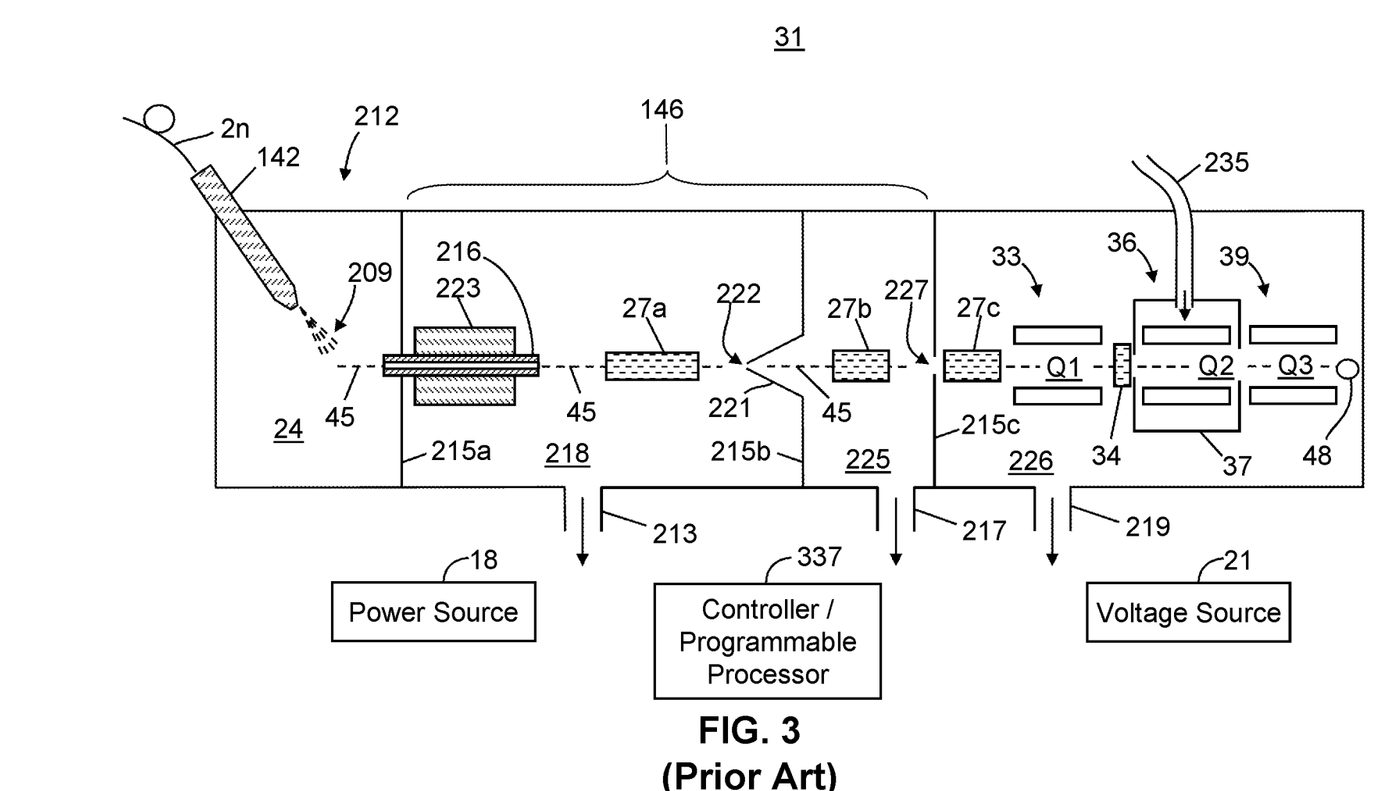
FIG. 3 is a schematic illustration of a conventional mass spectrometer system which may be employed in conjunction with the present teachings.

As shown in FIG. 2 as well as in FIG. 3, an atmospheric pressure ionization (either electrospray ionization ("ESI"), heated electrospray ionization ("H-ESI") or atmospheric pressure chemical ionization ("APCI")) device (referred to generally herein as "nebulizing ionizer") is used for ionizing the analytes received by the ionization source 212. In that regard, the nebulizing ionizer includes a capillary, probe, or needle (referred hereinafter as "needle" 142) having a solvent conduit therein (not shown) and surrounded by a gas conduit therein (not shown). An outlet of the gas conduit is positioned about 0.1 mm to about 0.2 mm proximally to an outlet of the solvent conduit.

In ESI operation a voltage generator 144 is electrically coupled to the needle 142 and is operable to create a high voltage difference between the needle 142 and the counter-electrode that may be at the mass spectrometer 31. A gas, typically an inert gas, such as nitrogen, is supplied to the gas conduit at pressures ranging from about 0 bar to about 7 bar. The voltage generator 144 is activated and provides a voltage potential, typically ranging from about −5 kV to about 5 kV, to the solvent within the needle 142. A skimmer 221 acts in conjunction with an auxiliary gas (not shown) to contain and/or focus the gas phase ions into a vacuum chamber of the mass spectrometer 31.

In alternative APCI operation, the voltage generator 144 is electrically-coupled to a corona discharge electrode 145 positioned distal to the outlets. An ion source that is switchable between ESI and APCI modes is described in co-pending U.S. application Ser. No. 13/280,069, titled "Combined Ion Source for Electrospray and Atmospheric Pressure Chemical Ionization" filed on Oct. 24, 2011, the disclosure of which is incorporated herein by reference in its entirety.

Referring still to FIG. 2, the illustrative example of the mass spectrometer 31 includes, in a basic embodiment, an interface 146 with the ionization source 212, a mass filter 33, and an ion detector 48. In many instances, the mass spectrometer 31 may also comprise a collision cell or fragmentation cell, as discussed further with reference to FIG. 3. The regions containing the mass filter 33 and the ion detector 48 are maintained under vacuum. This interface 146 includes an orifice or aperture 227 that provides an opening into a higher vacuum chamber containing the mass filter 33 while maintaining vacuum pressures.

In the illustrated example, the mass filter 33 is shown to be a conventional quadrupole; however, those skilled in the art will understand the determination by which the appropriate mass filter modality for a given assay is selected. In fact, other mass spectrometer embodiments may include, for example, a single quadrupole modalities, time-of-flight ("TOF"), Fourier Transform (FT), electrostatic trap or ion trap ("OT") modalities, or hybrid modalities, such as Q-TOF, TOF-TOF, Q-Exactive, LTQ-Oorbitrap, and LTQ-FT, or a mass spectrometer modified for proton transfer.

FIG. 3 is a more-detailed schematic illustration of an example of a general conventional mass spectrometer system 31 capable of providing tandem mass spectrometry in accordance with the methods disclosed herein. The mass spectrometer system 31 comprises an electrospray ion source (ESI) 212 having a needle 142 housed in an ionization chamber 24. The ESI needle 142 is connected so as to receive a liquid comprising analyte compounds from the chromatography sub-system 5 (or either one of the chromatography sub-systems 5a or 5b) through fluid tubing line 2n. The electrospray ion source 212 forms charged particles 209 (either free ions or charged liquid droplets that may be desolvated so as to release ions) representative of the sample. The emitted droplets or ions are entrained in a background or sheath gas that serves to desolvate the droplets as well as to carry the charged particles into a first intermediate-pressure chamber 218 which is maintained at a lower pressure than the pressure of the ionization chamber 24 but at a higher pressure than the downstream chambers of the mass spectrometer system. The ion source 212 may be provided as a "heated electrospray" (H-ESI) ion source comprising a heater that heats the sheath gas that surrounds the droplets so as to provide more efficient desolvation. The charged particles may be transported through an ion transfer tube 216 that passes through a first partition element or wall 215a into the first intermediate-pressure chamber 218. The ion transfer tube 216 may be physically coupled to a heating element or block 223 that provides heat to the gas and entrained particles in the ion transfer tube so as to aid in desolvation of charged droplets so as to thereby release free ions.

The free ions are subsequently transported through the intermediate-pressure chambers 218 and 225 of successively lower pressure in the direction of ion travel. A second plate or partition element or wall 215b separates the first intermediate-pressure chamber 218 from the second intermediate-pressure chamber 225. Likewise, a third plate or partition element or wall 215c separates the second intermediate-pressure region 225 from the high-vacuum chamber 226 that houses a mass analyzer 39 component of the mass spectrometer system. A first ion optical assembly 27a provides an electric field that guides and focuses the ion stream leaving ion transfer tube 216 through an aperture 222 in the second partition element or wall 215b that may be an aperture of a skimmer 221. A second ion optical assembly 27b may be provided so as to transfer or guide ions to an aperture 227 in the third plate or partition element or wall 215c and, similarly, another ion optical assembly 27c may be provided in the high vacuum chamber 226 containing a mass analyzer 39. The ion optical assemblies or lenses 27a-27c may comprise transfer elements, such as, for instance a multipole ion guide, so as to direct the ions through aperture 222 and into the mass analyzer 39. The mass analyzer 39 comprises one or more detectors 48 whose output can be displayed as a mass spectrum. Vacuum ports 213, 217 and 219 may be used for evacuation of the various vacuum chambers.

The mass spectrometer system 31 is in electronic communication with a controller or other programmable processor 337 which includes hardware and/or software logic for performing data analysis and control functions. Such controller or programmable processor may be implemented in any suitable form, such as one or a combination of specialized or general purpose processors, field-programmable gate arrays, and application-specific circuitry. In operation, the controller effects desired functions of the mass spectrometer system (e.g., analytical scans, isolation, and dissociation) by adjusting voltages (for instance, RF, DC and AC voltages) applied to the various electrodes of ion optical assemblies 27a-27c and quadrupoles or mass analyzers 33, 36 and 39, and also receives and processes signals from detectors 48. The controller 337 may be additionally configured to store and run data-dependent methods in which output actions are selected and executed in real time based on the application of input criteria to the acquired mass spectral data. The data-dependent methods, as well as the other control and data analysis functions, will typically be encoded in software or firmware instructions executed by controller. A power source 18 supplies an RF voltage to electrodes of the devices and a voltage source 21 is configured to supply DC voltages to predetermined devices.

As illustrated in FIG. 3, the mass spectrometer system 31 is a triple-quadrupole system comprising a first quadrupole device 33, a second quadrupole device 36 and a third quadrupole device 39, the last of which is a mass analyzer comprising one or more ion detectors 48. The first, second and third quadrupole devices may be denoted as, using common terminology, as Q1, Q2 and Q3, respectively. A lens stack 34 disposed at the ion entrance to the second quadrupole device 36 may be used to provide a first voltage point along the ions' path. The lens stack 34 may be used in conjunction with ion optical elements along the path after stack 34 to impart additional kinetic energy to the ions. The additional kinetic energy is utilized in order to effect collisions between ions and neutral gas molecules within the second quadrupole device 36. If collisions are desired, the voltage of all ion optical elements (not shown) after lens stack 34 are lowered relative to lens stack 34 so as to provide a potential energy difference which imparts the necessary kinetic energy.

Various modes of operation of the triple quadrupole system 31 are known. In some modes of operation, the first quadrupole device is operated as an ion trap which is capable of retaining and isolating selected precursor ions (that is, ions of a certain mass-to-charge ratio, m/z) which are then transported to the second quadrupole device 36. More commonly, the first quadrupole device may be operated as a mass filter such that only ions having a certain restricted range of mass-to-charge ratios are transmitted therethrough while ions having other mass-to-charge ratios are ejected away from the ion path 45. In many modes of operation, the second quadrupole device is employed as a fragmentation device or collision cell which causes collision induced fragmentation of selected precursor ions through interaction with molecules of an inert collision gas introduced through tube 235 into a collision cell chamber 37. The second quadrupole 36 may be operated as an RF-only device which functions as an ion transmission device for a broad range of mass-to-charge ratios. In an alternative mode of operation, the second quadrupole may be operated as a second ion trap. The precursor and/or fragment ions are transmitted from the second quadrupole device 36 to the third quadrupole device 39 for mass analysis of the various ions.

Figure 4:
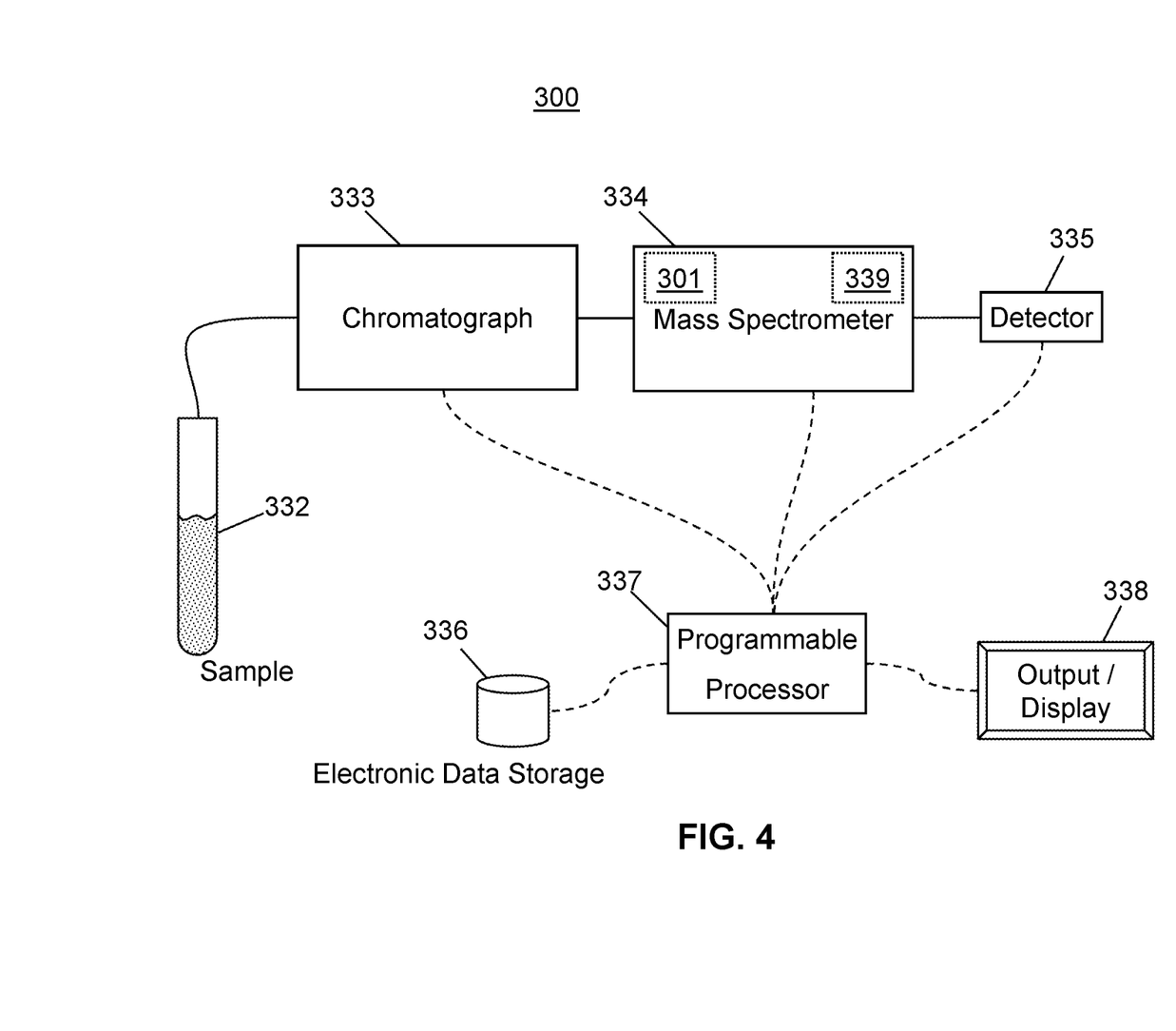
FIG. 4 is a schematic diagram of a system for generating and automatically analyzing chromatography/mass spectrometry spectra.

FIG. 4 is a schematic diagram of which summarizes the general components of a system 300 for generating and automatically analyzing chromatography/mass spectrometry spectra in accordance with the present teachings. A liquid chromatograph 333 receives a sample 332 of an analyte mixture and at least partially separates the analyte mixture into individual chemical constituents. In accordance with the present teachings, at least some of the chromatographic separations of the liquid chromatograph 333 are performed on immunosuppressant drug compounds using the columns 7a, 7b and methods as described herein. The least partially separated chemical constituents, including immunosuppressant drug analytes are transferred to a mass spectrometer 334 at different respective times for mass analysis. One non-limiting example of a mass spectrometer is illustrated, for instance, in FIG. 3. As each chemical constituent is received by the mass spectrometer, it is ionized by an ionization source 301 of the mass spectrometer. The ionization source 301 may produce a plurality of ions (i.e., a plurality of precursor ions) comprising differing charges or masses from each chemical component. Thus, a plurality of ion types of differing mass-to-charge ratios may be produced for each chemical component, each such component eluting from the chromatograph at its own characteristic time. These various ion types are analyzed and detected by the mass spectrometer together with its detector 335 and, as a result, appropriately identified according to their various mass-to-charge ratios. As illustrated in FIG. 4, the mass spectrometer comprises a reaction cell 139 to fragment or cause other reactions of the precursor ions.

Still referring to FIG. 4, a programmable processor 337 is electronically coupled to the detector of the mass spectrometer and receives the data produced by the detector during chromatographic/mass spectrometric analysis of the sample(s). The programmable processor may comprise a separate stand-alone computer or may simply comprise a circuit board or any other programmable logic device operated by either firmware or software. The programmable processor may also be electronically coupled to the chromatograph and/or the mass spectrometer in order to transmit electronic control signals to one or the other of these instruments so as to control their operation. The nature of such control signals may possibly be determined in response to the data transmitted from the detector to the programmable processor or to the analysis of that data. The programmable processor may also be electronically coupled to a display or other output 338, for direct output of data or data analysis results to a user, or to electronic data storage 336.

The programmable processor 337 may be electronically coupled to the valves v1, v2 and v3 so as to control their state at any time. The programmable processor 337 may be electronically coupled to the pumps 13a, 13b and 13c (FIG. 1A) or to the pump 13a and the syringe pumps 13d, 13e, 13f, 13g and 13h (FIG. 1B) so as to control the flow of liquids (solvents or solvents plus sample) through the tubing lines and columns at any time. The programmable processor 337 may also be electronically coupled to optional heaters (not shown) associated with the chromatographic columns 7a, 7b so as to control the operating temperatures of the columns. In general, a liquid chromatographic "test method" (or simply "method") comprises a sequence of timed steps during which the mixing of sample and solvents, the compositions of mobile phases and the flow directions and flow rates of sample and mobile phases through one or more chromatographic columns are controlled. Such test methods are frequently specific to certain assays. With regard to FIG. 1, FIG. 2 and FIG. 4, a method may be implemented as a sequence of programmed steps that caused the programmable processor 337 to control the configuration of valves and the operation of pumps in either the system 10 or the system 12. Such test methods may also control the temperatures of the chromatographic columns 7a, 7b by controlling the operations of associated heaters (not shown) in response to temperature readings provided to the programmable processor 337 by temperature sensors (not shown).

Example

Materials and Methods

The following chemicals, used as solvents and additives, were obtained from Fisher Scientific™ of Waltham, Mass., USA: acetonitrile (LC-MS grade), acetone (HPLC grade), methanol (LC-MS grade), isopropanol (HPLC grade), water (LC-MS grade), ammonium hydroxide, formic acid, and zinc sulfate heptahydrate, 99%. A stock solution of tacrolimus-$^{13}CD_2$, used as an internal standard, was obtained from Toronto Research Chemicals. A stock solution of $D_{12}$-cyclosporin A, used as a second internal standard, was obtained from Alsachim.

A neat tacrolimus internal standard solution was prepared at a concentration of 1000 ng/mL by mixing 20 uL of the stock solution in 20 mL of methanol. A neat cyclosporin A internal standard solution was prepared at a concentration of 10000 ng/mL by mix 200 uL of the stock solution in 20 mL of methanol. The internal standard solutions were stored at a temperature of −20° C. or lower until needed. An aqueous zinc sulfate solution for lysing blood cells was prepared at a concentration of 0.1 mM by dissolving 0.288 g of zinc sulfate heptahydrate in 1000 mL of water.

Lyophilized products of ChromSystems™ 6PLUS1™ multilevel whole-blood calibrator set and ChromSystems™ MassCheck™ immunosuppressants whole blood controls were prepared according to the manufacturer's package inserts. When performing test assays, a precipitation solution containing 15 ng/mL of tacrolimus internal standard and of 150 ng/mL cyclosporin A internal standard was prepared by mixing 1.5 mL of the neat tacrolimus internal standard solution and 1.5 mL of the neat cyclosporin A internal standard solution with 100 mL of methanol. Table 1 lists typical concentrations in ng/mL of calibrator (Cal) and quality control (QC) materials of the investigated immunosuppressant drugs, as per the manufacturer's labeling.

During sample preparation, whole blood calibrators, quality controls and test samples were mixed with aqueous zinc sulfate solution and then with methanol containing internal standards. Specifically, 300 μL of the 0.1 mM aqueous $ZnSO_4$ solution was added to 200 μL of each whole blood sample in a respective micro-centrifuge tube so as to cause blood cells to rupture and some proteins to precipitate, after which the samples in the tubes were vortex mixed for 30 seconds. Subsequently, in order to complete protein precipitation and introduce the internal standards, 500 μL of the internal-standard-containing precipitation solution was added to each tube and the samples were vortex mixed for another 30 seconds. After vortexing, the tubes were centrifuged at 4000 relative centrifugal force (RCF) for 5 minutes or longer to ensure a stable pellet. The clean supernatant with was then withdrawn for LCMS analysis.

TABLE 1

Immunosuppressant calibrator and QC concentrations (ng/mL)

|  | Everolimus | Sirolimus | Tacrolimus | Cyclosporin A |
|---|---|---|---|---|
| Cal 1 | 2.4 | 2.6 | 2.5 | 43 |
| Cal 2 | 5.8 | 6.5 | 6 | 127 |
| Cal 3 | 10.7 | 11.8 | 11.1 | 290 |
| Cal 4 | 15.4 | 17.5 | 16.3 | 464 |
| Cal 5 | 21.5 | 26 | 22.9 | 738 |
| Cal 6 | 38.4 | 43.4 | 39.6 | 913 |
| QC I | 2.3 | 2.9 | 2.6 | 53 |
| QC II | 4.4 | 10.1 | 7.3 | 276 |
| QC III | 8.5 | 20.4 | 16.7 | 514 |
| QC IV | 28.8 | 38.5 | 34.2 | 1111 |

Analyses of the test samples prepared as described above were performed by the technique of LC-MS/MS using a system of the type shown in FIG. 1 which did not include a guard column and which was employed as a component of a Prelude™ automated liquid chromatography system available from Thermo Scientific of Waltham, Mass. USA. The system uses syringe pumps with 3 mL internal volumes designed for a single push per sample analysis, yielding extremely low dead volumes and low solvent usage. For this example, the Prelude™ LC system processed 20 μL injections of each supernatant prepared as described above. The two columns (i.e., column 7a and column 7b in FIG. 1) employed in this example comprised, respectively, a Cyclone-P™ TurboFlow™ column, which performed initial sample clean-up, and an Accucore™ C8 analytical column (3.0×30 mm) in which the analytes were separated, and then eluted. Built-in column heaters maintained the analytical columns at 70° C. Similar to the apparatus shown in FIG. 2, the Prelude LC system incorporates two channels that can be multiplexed to the MS/MS system to double sample throughput.

The eluting analytes were detected and quantified using a TSQ Vantage™ tandem mass spectrometer (MS/MS) with heated electrospray ion (HESI-II) source (commercially available from Thermo Scientific) operating in positive ionization mode. Isotope-dilution quantitation was accomplished using selective reaction monitoring (SRM) of four ISDs and two internal standards. For detecting and quantifying tacrolimus, monitoring was performed of the fragment ion at mass-to-charge ratio (m/z) 768.5 as generated from the precursor ion at m/z 821.5; in other words, the monitored SRM transition may be represented as 821.5→768.5. For detecting and quantifying sirolimus, everolimus and cyclosporin A, the monitored transitions were 931.6→864.6, 975.7→008.4 and 1202.8→425.3, respectively. The monitored transitions for the tacrolimus and cyclosporine A internal standards were 824.4→771.0 and 1214.9→437.2, respectively. In one set of experiments, transitions for the common phospholipids lyso-phosphotidylcholine 16:0 (transition 496→184) lyso-phosphotidylcholine; 18:0 (transition 524→184) and phosphotidylcholine; 38:6 (transition 806→184) were also monitored in order to determine their effects on the ISD analyses.

In this example, mobile and stationary phases as well as column geometry were optimized to minimize the extraction and accumulation of phospholipids in the LC-MS/MS system and to separate residual phospholipids from the ISDs. The Prelude™ LC system included a provision for employing reservoirs of five different mobile phase compositions. In this example, three different mobile phase reservoirs were employed as follows: "Mobile Phase A" (MPA) consisted of water+10 mM ammonium formate+0.05% formic acid; Mobile Phase B" (MPB) consisted of methanol+10 mM ammonium formate+0.05% formic acid; "Mobile Phase C" (MPC) consisted of 400 mL of acetonitrile with 400 mL of 2-propanol and 200 mL of acetone. During chromatography, samples were filled into the looped tubing 2c using MPB. Samples were then transferred into the TurboFlow column (7a) using a mobile phase comprising a mixture of 70% of MPA and 30% of MPB. The analytes were then transferred out of the Turboflow column and focused onto the Accucore analytical column (7b) using the same mixture of 70% of MPA and 30% of MPB.

After the analytes were transferred to the analytical column, the separation and elution of the analytes was accomplished by changing the composition of the mobile phase introduced into the analytical column. In this regard, the present method differs from a known prior ISD assay method that employs flow of 100% MPB over the course of the final seventy-five percent of the analyte separation and elution time. With the present method, in order to separate and elute analytes using the shorter (30 mm) column, the composition of the mobile phase introduced into column 7b was initially step-wise changed so as to comprise a mixture of 30% of MPA and 70% of MPB. This mobile phase composition was then changed to 100% MPB in a gradual fashion over the course of analyte separation and elution such that only the final fifteen percent of the separation and elution time corresponded to 100% MPB mobile phase composition. After elution, the analytical column (7b) was washed with 100% MPB. Simultaneously with elution, the TurboFlow column (7a) was washed with each of 100% MPC, 100% MPA and 100% MPB.

EXPERIMENTAL RESULTS AND CONCLUSIONS

Use of the above-described method resulted in improved reproducibility of peak areas for the internal standards $D_{12}$-Cyclosporin A and Tacrolimus-$^{13}CD_2$ as well as for peak areas for everolimus, sirolimus, tacrolimus and cyclosporin A at their limits of quantitation. For example, it was found that the relative standard deviation (RSD) of these peak areas was routinely 10% or better. Consequently, one stable isotope-tacrolimus-$^{13}CD_2$—was sufficient for reliable quantitation of tacrolimus, everolimus and sirolimus, while $D_{12}$-Cyclosporin A served as a reliable internal standard for cyclosporin A. Further, the calibrations were using the whole-blood calibrators were found to be highly linear. Using 1/x weighting, the correlation coefficients ($r^2$) were typically found to be greater than 0.995 for calibrations of: cyclosporin A, from 25 to 1250 ng/mL, and everolimus, sirolimus and tacrolimus, from 2.5 to 50 ng/mL. Additional reliability and economy were realized from the use of a novel pumping design and fluidics configuration of the liquid chromatography system, which improved retention time reproducibility and minimized solvent waste.

The results from the experiments that included monitoring of phospholipid transitions indicated that most of the variability in peak areas among internal standards were due to phospholipid co-elution. Nonetheless, the internal standards do a good job of compensating for such interferences provided that the proportion of phospholipids relative to analytes is not artificially increased by sample-to-sample carryover of the phospholipids. Prior experiments have shown that the phospholipids wash away much more readily from smaller (3.0×30 mm) analytical columns, avoiding buildup and subsequent carryover of such interferences. The present results indicate that the C8 stationary phase in the Accucore™ 30 mm column provides the selectivity needed to separate small amounts of phospholipids from the ISDs. Other stationary phases—C18, PFP and aQ—did not work as well as C8. Further, with regard to analyte carryover, it was found from the present experimental results that the peak areas corresponding to the tacrolimus internal standard and the cyclosporin A internal standard in blank post injections are typically less than 0.1% of those from the injections of the working precipitation solution containing these internal standards.

The low dwell volumes of the syringe pumps employed in the LCMS system result in more rapid delivery of solvent changes (i.e., the gradient profile) to the column, thereby reducing the total run time and, therefore, increasing sample throughput. The dwell volume of the pumping system needs to be small if the flow rate to the analytical column is slow. When using electro-spray ion sources, such slow flow rates result in better sensitivity, as slow flows provide optimum droplet formation resulting in a higher percentage of analytes getting ionized.

The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the scope and essence of the invention. Neither the description nor the terminology is intended to limit the scope of the invention. Any patents, patent applications, patent application publications or other literature mentioned herein are hereby incorporated by reference herein in their respective entirety as if fully set forth herein.

What is claimed is:

1. A method for assaying one or more immunosuppressant drug analytes in a sample comprising a supernatant fluid of lysed whole blood, the method comprising:
    (a) passing the sample dissolved in a mobile phase through a length of 30 mm or less of a stationary phase of a reversed-phase chromatographic column so as separate the analytes from one another;
    (b) eluting the separated analytes from the reversed-phase chromatographic column;
    (c) ionizing molecules of the eluted separated analytes by a heated electrospray ionization source of a mass spectrometer so as to generate a plurality of precursor ion species;
    (d) isolating, for each analyte, a respective one of the precursor ion species;
    (e) fragmenting ions of each of the isolated precursor ion species in a fragmentation cell of the mass spectrometer so as to generate a plurality of product ions therefrom; and
    (f) detecting, for each analyte, the presence and quantity of a respective one of the product ion species using a detector of the mass spectrometer.

2. A method as recited in claim 1, wherein the step (a) comprises passing the sample dissolved in the mobile phase through a stationary phase comprising an 8-carbon alkyl chain material bonded to 2.6 µm diameter particles having solid silica cores surrounded by porous silica outer layers.

3. A method as recited in claim 1, wherein the step (a) comprises passing the sample dissolved in the mobile phase through a length of 30 mm or less of a stationary phase comprising an 8-carbon alkyl chain material bonded to 2.6 µm diameter particles having solid silica cores surrounded by porous silica outer layers.

4. A method as recited in claim 3, wherein the mobile phase comprises a mixture of a first solvent (MPA) comprising water+10 mM ammonium formate+0.05% formic acid and a second solvent (MPB) comprising methanol+10 mM ammonium formate 0.05% formic acid, wherein the composition of the mobile phase mixture varies from 30% MPA and 70% MPB to 0% MPA and 100% MPB during the separating and eluting of the analytes.

5. A method as recited in claim 4, further comprising washing the reversed-phase chromatographic column with the MPB solvent to remove phospholipids from the column.

6. A method as recited in claim 1, further comprising passing the sample into and out of a high turbulence liquid chromatography column prior to performing the step (a) so as to remove non-analyte compounds from the sample.

7. A method as recited in claim 1, wherein the one or more analytes comprise one or more of the compounds everolimus, sirolimus, tacrolimus and cyclosporin A and wherein the method further comprises adding internal standards $^{13}CD_2$-tacrolimus and $D_{12}$-cyclosporin A to the sample prior to performing the step (a) and wherein the method further comprises monitoring the presence of the internal standards using the mass spectrometer.

8. A method as recited in claim 7, wherein an analyte is tacrolimus and the steps (d) and (e) comprise isolating and fragmenting precursor ions having a mass-to-charge ratio (m/z) of 821.5 and the step (e) comprises detecting the presence and quantity of tacrolimus by monitoring fragment ions having an m/z of 768.5 generated by fragmentation of the precursor ions having m/z of 821.5.

9. A method as recited in claim 7, wherein an analyte is sirolimus and the steps (d) and (e) comprise isolating and fragmenting precursor ions having a mass-to-charge ratio (m/z) of 931.6 and the step (e) comprises detecting the presence and quantity of sirolimus by monitoring fragment ions having an m/z of 864.6 generated by fragmentation of the precursor ions having m/z of 931.6.

10. A method as recited in claim 7, wherein an analyte is everolimus and the steps (d) and (e) comprise isolating and fragmenting precursor ions having a mass-to-charge ratio (m/z) of 975.7 and the step (e) comprises detecting the presence and quantity of everolimus by monitoring fragment ions having an m/z of 908.4 generated by fragmentation of the precursor ions having m/z of 975.7.

11. A method as recited in claim 7, wherein an analyte is cyclosporin A and the steps (d) and (e) comprise isolating and fragmenting precursor ions having a mass-to-charge ratio (m/z) of 1202.8 and the step (e) comprises detecting the presence and quantity of cyclosporin-A by monitoring fragment ions having an m/z of 425.3 generated by fragmentation of the precursor ions having m/z of 1202.8.

\* \* \* \* \*